United States Patent [19]

Haverstock

[11] Patent Number: 4,531,521

[45] Date of Patent: Jul. 30, 1985

[54] SKIN CLOSURE MEANS

[76] Inventor: Charles B. Haverstock, 44 Frederick La., Glendale, Mo. 63122

[21] Appl. No.: 471,718

[22] Filed: Mar. 3, 1983

[51] Int. Cl.³ .............................................. A61B 17/08
[52] U.S. Cl. ..................................................... 128/335
[58] Field of Search ............. 128/335, 155, 156, 334 R

[56] References Cited

U.S. PATENT DOCUMENTS

| 2,196,296 | 4/1940 | Flynn | 128/335 |
| 2,762,371 | 9/1956 | Guio | 128/335 |
| 3,698,395 | 10/1972 | Hasson | 128/335 |
| 3,863,640 | 2/1975 | Haverstock | 128/335 |
| 4,141,363 | 2/1979 | James et al. | 128/335 |
| 4,423,731 | 1/1984 | Roomi | 128/335 |

Primary Examiner—C. Fred Rosenbaum
Assistant Examiner—C. W. Shedd
Attorney, Agent, or Firm—Haverstock, Garrett & Roberts

[57] ABSTRACT

Improvements in skin closures that unite and hold separable closure members and skin portions attached thereto accurately together to prevent separation thereof by forces which might otherwise cause the united members to separate, the improvement including sheet members adhesively attached on opposite sides of a skin separation or incision and one or more folded back sheet portions or separate sheet elements for use in adhesively connecting the sheet members about the skin separation or incision thereby closing the skin separation or incision. In addition, the improvement includes protective coverings over the adhesive layers for use in protecting the adhesive until such time as it is necessary to utilize the skin closure. The improvement also can include elements to aid in accurately guiding a scapel as it makes an incision through the skin closure to aid in preventing damage to the skin closure that would impair its ability to function as such.

15 Claims, 13 Drawing Figures

SKIN CLOSURE MEANS

This application discloses further improvements on the skin closures disclosed in my U.S. Pat. Nos. 3,863,640, 3,933,158, and 4,114,624. In those patents I disclose various embodiments of skin closures by which the separated side edges of a skin injury, wound, incision, laceration, or the like can be accurately aligned, closed, and held after closure in the most advantageous position to facilitate healing with a minimal possibility of scar tissue formation. Such devices are useful in situations where there is no access to medical assistance, and the prior constructions also have applications in surgical procedures as well as under emergency medical treatment procedures where time is limited and where other suturing means may be unavailable. The present means are believed to be superior to known forms of suturing and stapling in many cases. They are also useful in emergency situations such as in catastrophes and in wartime where there is a great need to be able to quickly, simply and accurately close injuries or skin separations for purposes readily apparent to those skilled in emergency treatment. The present device is also useful in post-mortem surgical procedures such as autopsies and the embalming of the dead since means are provided for rapidly providing a leak-proof seal along incisions and skin separations, including incisions and skin separations of substantial length. Thus, the present construction substantially reduces or eliminates the need for suturing and stapling and is also useful as a means for preventing the formation of scar tissue. It is recognized, however, that when used in conjunction with a surgical procedure, especially where deep incisions are made, that some subcutaneous suturing may be required, but even in these situations the ability to be able to quickly and accurately close the incision at the skin surface may be brought about by use of closure means such as disclosed in this, and the above-referenced U.S. patents.

The preferred embodiment of the present device includes first and second sheet portions of a relatively thin, flexible material. Corresponding surfaces of each sheet portion have adhesive thereon for attaching them to the skin and one of the sheet portions has a flap portion that is folded back along one side edge thereof and adhesively attached to said one portion. The exposed surface of the folded back portion has an adhesive thereon enabling it to be attached to the second sheet portion, and removable cover layers for the adhesive layers on the first and second sheet portions.

This process of closing and bandaging is begun by removing the protective layer covering the adhesive on the corresponding surfaces of the first and second sheet portions and adhesively attaching the portions to the skin with a side edge of each portion extending along opposite side edges of a skin separation to be closed, and thereafter detaching the flap portion of the first portion and moving it across the second portion and when properly positioned relative thereto adhesively attaching it to the second sheet portion.

The present application discloses several different embodiments of skin closure devices which are particularly adaptable for emergency medical care use, although they may also be used in conjunction with a surgical procedure as will be explained.

It is a principal object of the present invention to provide means for accurately and quickly closing separated skin portions during emergency medical treatment, during surgical procedures, and during post-mortem surgical procedures.

Another object is to improve the healing conditions between separated skin areas along a break or tear in the skin and along incisions.

Another object is to reduce or eliminate the need for suturing and stapling the skin, particularly cutaneous suturing and stapling in medical and surgical procedures.

Another object is to minimize the formation of scar tissue and keloiding following the closing of incisions, lacerations, and other skin separations.

Another object is to teach the construction of skin closure means which are adaptable to being made in any lengths and widths and which can be trimmed to facilitate use as needed or desired depending upon the nature, location, and contour of the skin at the location where the incision or closure is to be made, or where the skin separation is found.

Another object is to reduce the time required to close a skin separation.

Another object is to teach the construction of skin closure means which can be applied to the skin and closed without requiring any special tools.

Another object is to provide an effective skin closure which can be removed when it has served its purpose like an ordinary adhesive bandage.

Another object is to provide means which enable accurate piecemeal closing of a skin separation.

Another object is to provide additional options for closing incisions in surgical procedures and the like.

Another object is to provide means that can be used to form leak-proof seals along skin separations including skin separations on deceased individuals.

Another object is to reduce the likelihood of tearing of skin tissue along a skin separation.

Another object is to provide a means for attaching to the skin along opposite sides of a skin separation to hold the skin separation open during surgery or otherwise.

Another object is to provide skin closure means which hold separated opposing skin portions together with equal and continuous or substantially continuous pressure along the entire length of the skin separation.

Another object is to reduce the pain involved in closing a skin separation and the subsequent removal of the closure means.

Another object is to teach a fast, simple, and effective method for closing a skin separation under emergency conditions.

Another object is to provide skin closure means which are relatively flat and smooth, and do not create a ridge to interfere with the wearing of clothes or to become irritated by friction with garments worn during the healing process or with bed clothes.

Another object is to provide skin closure means which also provide effective protection for the wound.

Another object is to teach the construction of a skin closure device that can be perforated or constructed of a mesh or an open webbing or netting material to expose at least some of the skin over the area where the device is attached to the atmosphere.

These and other objects and advantages of the present invention will become apparent after considering the following detailed specification which discloses several different embodiments of the subject construction in conjunction with accompanying drawings wherein:

3

Figure 1:
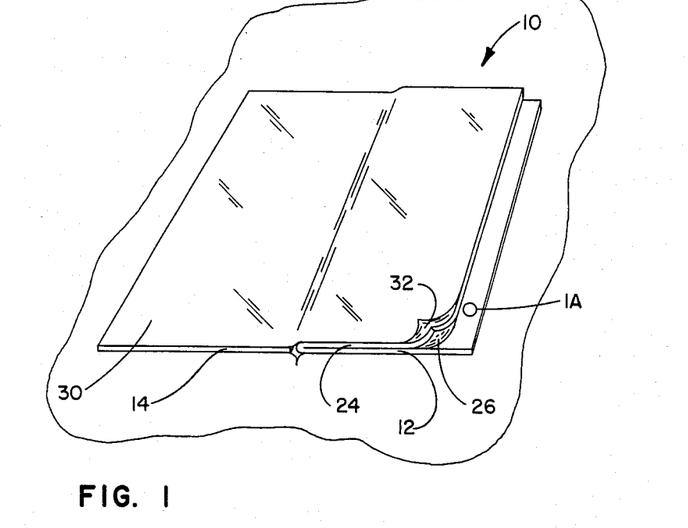
FIG. 1 is a perspective view of one embodiment of the subject closure means constructed according to the present invention, said means being shown adhesively attached to the skin.
Figure 1A:
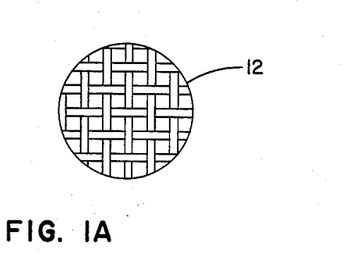
FIG. 1A is a greatly enlarged partial top plan view of the device of FIG. 1 showing the possibility of a mesh-like construction for the sheet portions.

Referring to the drawings more particularly by reference numbers wherein like numerals refer to like parts, number 10 in FIG. 1 indicates a skin closure device constructed according to one embodiment of the present invention. The embodiment 10 may be applied to the skin as a one piece construction prior to the making of an incision by a surgeon, or may be applied as separate halves in alignment with the opposite side edges of a skin separation as will be discussed hereinafter. In either case, the embodiment 10 is used to quickly and accurately close the skin separation and hold the opposite edges of the skin separation in alignment and in position to reduce the degree of scar tissue formation which is normally occasioned during the healing process. The device 10 includes two adjacent sheet portions 12 and 14 which are comprised of relatively thin, flexible and, if desired, transparent or transluscent material. Plastic or other similar material, including fabric, may be used in the construction. It is also preferable that the sheet portions 12 and 14 be constructed of breathable material, that is material that will permit at least some air to reach the skin surfaces to which they are attached. This can be accomplished by the selection of the material used, by perforating the material during the construction process or by a combination of these two methods. The sheet portions can also be constructed of a mesh, open webbing or netting material as shown in FIG. 1A to enable maximum exposure of the skin to the atmosphere when the device is attached.

Figure 2:
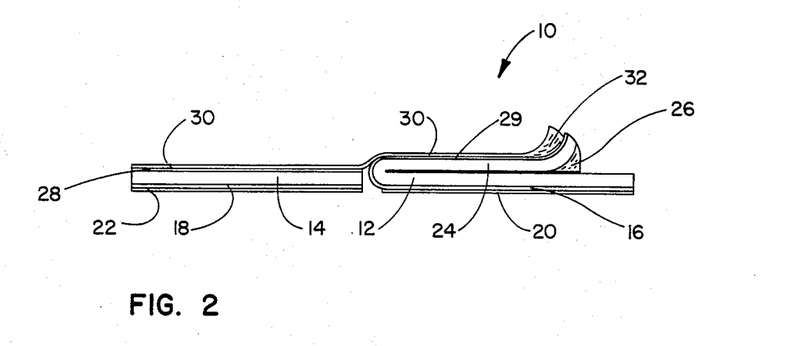
FIG. 2 is an enlarged end view of the device of FIG. 1 showing the details of the device as it is made and before it is used by being applied to the skin.

As shown in FIG. 2 layers of adhesive 16 and 18 are applied to the underneath or skin engaging surfaces of the sheet portions 12 and 14 respectively for attaching the device 10 to the skin along opposite side edges of a skin separation that is to be closed. Additionally, removable protective coverings 20 and 22 are placed over the adhesive layers 16 and 18 to protect them prior to application of the device 10 to the skin. A one piece covering member can also be used and is preferred in many situations to cover both adhesive layers 16 and 18, though the use of separate coverings is usually preferred when the device 10 is to be used in emergency medical situations where each sheet member is to be attached to the skin extending along opposite sides of an existing skin separation. If a one piece protective covering is used it can be provided with a line of perforations extending along where the portions 12 and 14 approximately abut to facilitate separating the two portions of the device prior to attachment to the skin. The thin protective coverings 20 and 22 are made of a suitable material such as a plastic, waxed paper, waxed plastic or like material.

The sheet portion 12 has an integral folded back flap portion 24 which is of the same material and construction as sheet portion 12, but is laid back against the upper or non-skin engaging surface of sheet portion 12 in position for later use in closing the separated skin portions as will be explained. The sheet portion 24 is temporarily adhesively or otherwise affixed to the upper surface of the sheet portion 12, such as by use of a small amount of adhesive. The adhesive can be placed at suitable locations such as at the corners of the sheet portion 24 as indicated by the location of item 26 as shown in FIGS. 1 and 2 or it can extend to cover more of the area between the portions 12 and 24 as desired. The important thing is to keep the portions 12 and 24 attached so that the portion 24 is out of the way until it is needed to close the skin separation.

Figure 3:
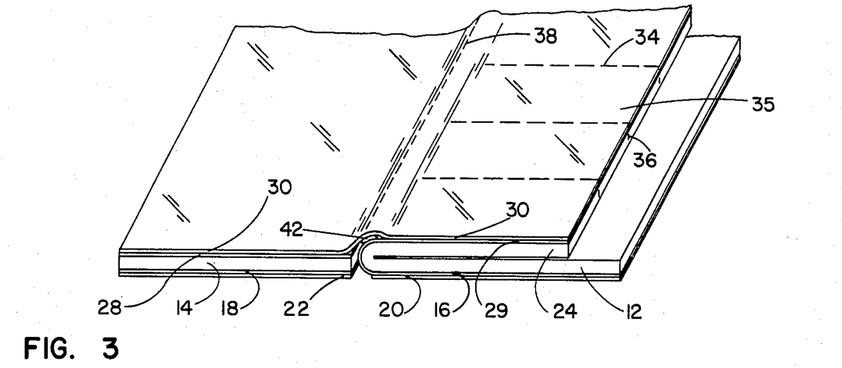
FIG. 3 is an enlarged fragmentary perspective view showing another embodiment of the subject closure means.
Figure 4:
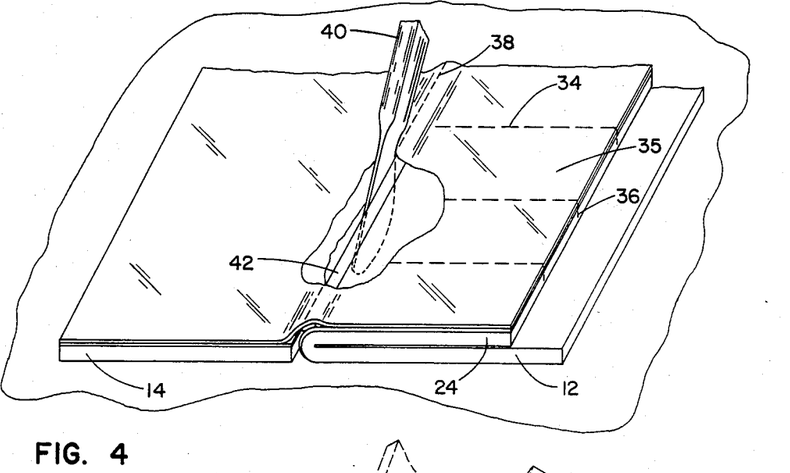
FIG. 4 is an enlarged fragmentary perspective view showing the device of FIG. 3 as an incision is being made, severing the device and the skin to which the device is attached.

The upper surface of sheet portion 14, and/or the folded back upper surface of the sheet portion 24 are covered or coated with other layers of adhesive material such as layers 28 and 29 as shown in FIG. 2 which are useful when needed to hold a skin separation together as will be explained. The layers 28 and 29 cover as much as necessary of the upper surfaces of sheet portions 14 and 24. The skin closure 10 is also provided with an upper protective covering 30, similar to the protective coverings 20 and 22, which extends to cover the adhesive layers 28 and 29, and these coverings remain in place until removed to close a skin separation. The protective covering 30 may be made of any material such as those mentioned above including a waxed paper or plastic. Additionally, the protective covering 30 as well as other protective coverings may have one or more corner tabs as at 32 in FIGS. 1 and 2 which are not adhered to the adhesive layer and are provided to facilitate gripping the protective covering during removal. The protective covering 30 as well as the portion 24 may also be provided with one or more transverse perforations or slits as at 34 and 36, as shown in FIGS. 3 and 4 which enable the user to separate the portion 24 into segments 35 for attaching one at a time progressively as the device is used to close a skin separation. Additionally, the protective covering 30 preferably extends over the adhesive on the entire upper surfaces of the device 10 to include the upper surface of the portion 14 and the upper surface of the folded back portion 24. This facilitates attaching the entire device 10 to the skin as a one piece construction after the coverings 20 and 22 for the lower surfaces are removed as when the embodiment 10 is attached prior to surgery. The protective layer or covering 30 may also be perforated as at 38 as shown in FIGS. 3 and 4 along the length of the device at the location where the portions 12 and 14 abut to facilitate separating or cutting the covering 30 while it is still attached during the making of an incision between the portions 12 and 14. The perforations 38 can also be used to provide the surgeon with a guide for his scalpel to facilitate making an incision which may be an advantage since it will not then be necessary to apply much, if any, force to cut through the closure device 10 when the incision is made.

Figure 5:
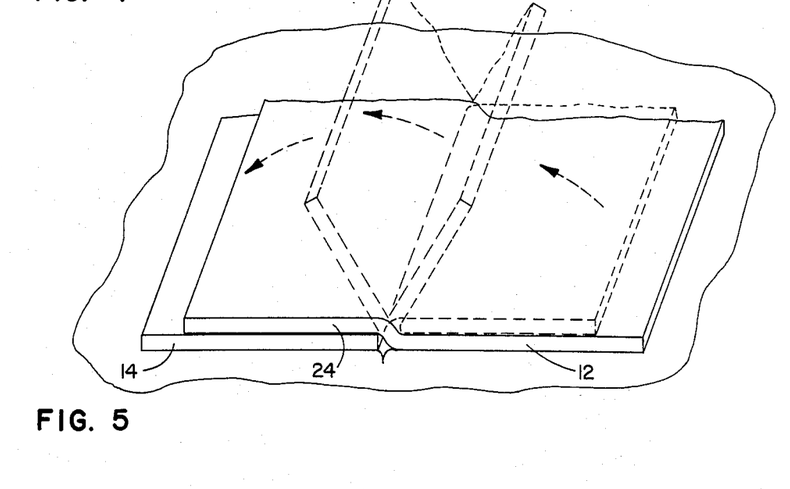
FIG. 5 is an enlarged fragmentary perspective view of the embodiment shown in FIG. 3, showing the device adhesively attached to the skin and indicating by use of dotted lines the progressive motion employed in using the device to close a skin separation.

The embodiment 10 may be used in an emergency medical treatment procedure to quickly and accurately close an existing skin separation by first separating the two halves of the embodiment 10, or sheet portions 12 and 14. This can be accomplished by cutting through the upper protective covering 30 along the center line, or, if perforations 38 are provided, by applying sidewise pressure to separate the portions 12 and 14 along the line of perforations. This can be done before or after the device is adhesively attached to the skin. If done before attachment to the skin, then the lower protective covering 20 on sheet portion 12 is removed to expose adhesive layer 16. The sheet portion 12 is then aligned with the edge of the skin separation or with where the incision is to be made. Next, the sheet portion 12 is adhered to the skin using the adhesive layer 16. Similarly, protective covering 22 on sheet portion 14 is removed to expose adhesive layer 18, and the edge of sheet portion 14 is aligned with the opposite side edge of the skin separation or incision in a position to be adjacent the edge of the folded back sheet portion 24 when the skin separation is closed. Once aligned, the sheet portion 14 is also adhered to the skin. After the sheet portions 12 and 14 are both adhered to the skin and it is desired to close the skin separation, the upper protective covering 30 over each sheet portion is removed exposing adhesive layers 28 and 29. Folded back sheet portion 24 is then detached from sheet portion 12 by pulling up on it and thereafter it is pulled and if necessary stretched over and towards the opposite or far edge of the sheet portion 14 as shown in FIG. 5. This enables the edges of the portions 12 and 14 as well as the edges of the skin separation to be brought into abutment, and thereafter the portion 24 is adhered to the sheet portion 14 by pressing it down thereon to adhere the adhesive layers 28 and 29 to each other. Preferably, minimal pressure is required so that there is little chance for discomfort.

As is noted in FIGS. 3 and 4, the upper protective covering 30 may be provided with one or more transverse perforations or slits 34, and similarly the folded back sheet portion 24 likewise may be provided with one or more aligned transverse perforations or slits 36 at the same spaced locations as the slits 34 to enable the user to attach individual segments 35 of the sheet portion 24 to the sheet portion 14 so as to enable closing a skin separation or incision in a series of steps. Use of such perforations 34 and 36 facilitates closing a skin separation piecemeal, in an accurate, easy to control manner, and without having to expose all of the adhesive in the layer 29 on the member 24 at one time. This can be an advantage especially when closing relatively long skin separations as in certain surgical procedures and in post-mortem procedures. Additionally, the use of the transverse perforations or slits 34 and 36 may facilitate and accommodate the use of drain tubes and other similar devices commonly used in surgery. If necessary, portions of the device also can be trimmed to accomodate such devices and this is relatively easy to do with all forms of the present device.

When the embodiment 10 is to be used in a surgical procedure, the protective coverings 20 and 22 are removed, and the device is accurately located and adhesively attached to the skin at the location where the surgeon intends to make the incision. The location where the incision is to be made is the location along the abutment between the separate portions 12 and 14.

The device 10 also may be constructed to include means to guide a scapel such as scapel 40 shown in FIG. 4 when making an incision so as not to accidentally cut through portions of the device itself that are adhesively attached to the skin. If such an accidental cut occurred, and especially if the edge of the folded over portion 24 were cut through, it could adversely affect the ability to properly and accurately reclose the skin separation at the conclusion of surgery. To obviate this possibility, it is proposed for those devices that are to be attached to the skin prior to surgery, to provide a relatively hard, but somewhat resilient, scapel guide member 42 as shown in FIGS. 3 and 4 positioned extending along the device at the location of the fold where the folded back sheet portion 24 is connected to the portion 12. The member 42 will be held in position between the upper covering member 30 and the adhesive surface 29 on the portion 24 such that when the scapel 40 is used to make the incision it will cut through the covering member and into the flesh, being guided during the process by the guide member 42. After the incision is completed the guide member 42 will be exposed along the edge of the member 24 where, if desired, it can be easily grasped and removed for disposal. The member 42 can be constructed of a material such as aluminum, plastic, or some other material having similar characteristics for protecting the folded back portion from being cut. Once the member has been removed the covering layer 30 on the portion 24 can be reattached to the adhesive adjacent the former location of the removed member 42 until the surgery is completed or the portion of the covering along the incision can remain loose to facilitate taking hold of it and removing the covering at the conclusion of surgery. A guide member similar to the member 42 can be provided along both sides of the device, but this is usually not necessary.

The device 10 can be made in any desired length and width and also can be attached as a series of adjacent closures if desired. In addition, the device 10 can be perforated along the place where the incision is to be made so that little or no cutting action is required to sever the device when the incision is made. Once the incision is made and the surgical procedure accomplished, any subcutaneous suturing that is needed can be performed and thereafter the skin separation along the incision can be closed quickly and accurately in a manner similar to that previously described. During closure of the skin separation the folded back sheet portion 24 can be accurately manipulated to realign the edges of the skin separation in order to bring back into alignment even the very cells that were separated during the making of the incision, thereby reducing the chance for scar tissue formation which is normally occasioned during the healing process. This presents a far superior, more accurate, less time-consuming and less painful way to close a skin separation than is available by known methods such as by suturing and stapling. Also closure using the present device can be made much faster and easier than by known means and methods thereby substantially reducing the time required by the surgeon in the reclosing of the skin. Furthermore, skin closure using the present device results in a substantially flat body closure and one that naturally follows the contour of the skin in the area of the incision and one that more accurately closes the skin separation than is possible using the known means and methods mentioned above. Furthermore, the present device accomplishes this result without creating any projections or ridges along the skin separation that can rub on clothing, including bed clothing and other items, and produce discomfort. Therefore the healing process for patients having the subject means applied to them is expected to be more comfortable than the healing process for patients with skin separations closed by other means. Furthermore, the absence of ridges along the incision not only reduces the formation of scar tissue but also has the other advantages indicated.

It is also important that when the subject device 10 is adhered to dry skin prior to surgery, it can facilitate holding the skin in the best possible position and minimize tearing of the skin during surgery. Additionally, if desired, clamps or similar devices can be attached to the device 10 to hold the incision open during surgery, and the present device will provide better support for attaching clamps for this purpose than will the skin itself, and therefore will reduce the possibility for injury or damage such as skin tears and the like. Finally, the device 10 can be perforated or formed of a porous or open netting material which makes it possible for the skin to breathe where the device is attached and enables the device to be easily removed by applying a suitable solvent or the like which will reduce the gripping action of the adhesive once healing is completed. This is obviously not possible with conventional suturing and stapling. Also, as indicated, the present device can be used to great advantage in post-mortem surgical procedures such as in autopsies and the like and will provide unique advantages not only of providing the pathologist with a rapid means for closing incisions including large body incisions but it can also be used to provide leak-proof seals over the areas where the incisions are made to prevent the leakage of body fluids and accompanying soiling of the garments worn by the deceased.

Figure 6:
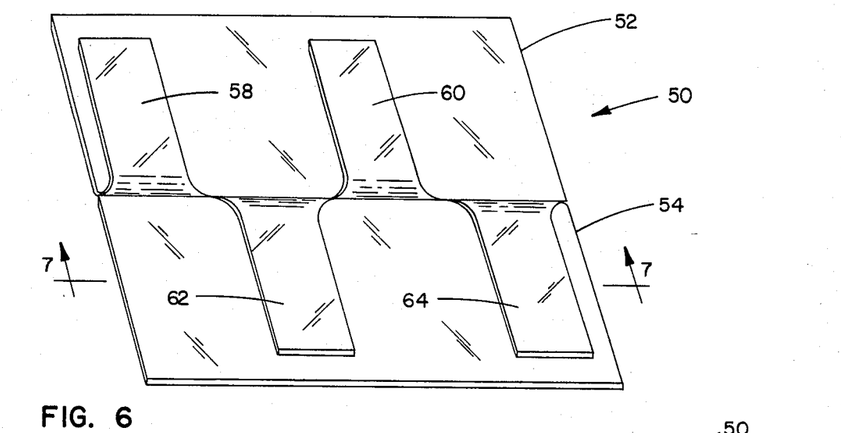
FIG. 6 is a perspective view showing another modified form of the present device.
Figure 7:
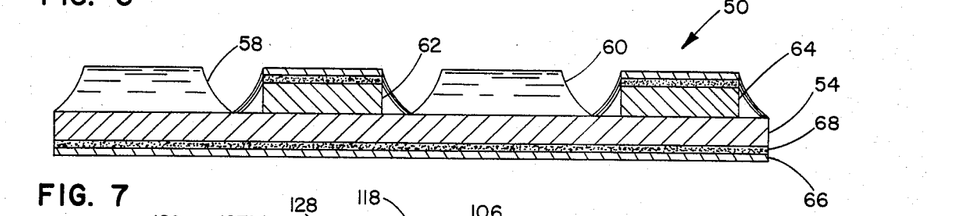
FIG. 7 is an enlarged cross-sectional view taken on line 7—7 of FIG. 6.

FIG. 6 shows another embodiment 50 of the subject construction which is similar in many respects to the embodiment 10 including having two adjacent connected sheet members 52 and 54, each of which has spaced folded back sheet portions 58 and 60, and 62 and 64 respectively. The folded back sheet portions 58 and 60 on the member 52 and the folded back portions 62 and 64 on the member 54 are staggered so that they are not opposite to one another along the device. As will be explained, this is important to the use of the structure 50 since it is desired when using the construction 50 to be able to close a skin separation piecemeal, that is, by attaching one or several of the folded back portions 58-64 to the opposite member starting at any desired location along the members and working in either direction. For example, the skin separation can be closed by starting at one end of the members 52 and 54 and closing the separation by attaching one or more of the folded over portions in order from one end to the other. It is also contemplated to attach two opposite but adjacent folded over portions at the same time as by separating them from the members to which they are attached and then by pulling them, somewhat like pulling shoelaces, to close the skin separation thereat. This procedure can be repeated along the device to close other pairs of folded over portions to completely close the separation. It will be apparent that the width of the folded over portions 58-64 can vary considerably so that relatively small sections of the skin separation can be closed at one time or the folded over portions can be made to be relatively wide so that relatively large portions of the skin separation can be closed at one time. The operation of the modified construction 50 is substantially similar to the operation of the constructions described above. For example, it can be attached to dry skin prior to surgery in which case the surgery will take place between the members 52 and 54 or it can be attached along a wet skin separation as in the case of field use to close a separation. In either case the operation will be substantially the same, that is, the lower covering layer or layers such as covering layer 66 shown in FIG. 7 is first removed from each of the portions 52 and 54 exposing the adhesive 68 to make the attachment to the skin, and thereafter the covering layers located on the upper folded over portions and/or on the portions of the opposite members to which the folded over portions are to be attached are removed to expose the adhesive layers thereunder so that the adhesive attachment can be completed. It is further anticipated that if a proper selection of adhesive is made then the adhesive connections along the separation can be reopened as desired to inspect the injury or to draw the members closer together or to make some other adjustment as required. The embodiment 50 therefore differs from the embodiment 10 in that the folded back sheet portions do not extend the entire length of either portion of the device but rather leave gaps along each device into which the folded over portions can be positioned to make the attachment. If the device 50 is attached to dry skin prior to surgery the lower covering 66 may extend over the entire lower surface of the device so that when the covering 66 is removed the entire device can be attached to the dry skin and the incision made at the location indicated between the members 52 and 54. However, if the device is to be attached to close an existing skin separation then care may be required to make sure that the overlapping portions 58-64 are staggered as indicated. If this should be a problem, then one could employ a series of closure means constructed according to the teachings of embodiment 10, each such closure being adhered to the skin approximately adjacent the previously placed closure. Generally, however, this will not be a difficult procedure and it may be possible in some cases to make the folded over portions of embodiment 50 narrower than the portions to which they are attached, thereby leaving some gaps between the areas of attachment. Generally this will not be a disadvantage if the gaps are not too long. Even a construction that provides some gaps is a marked improvement over conventional closure means such as suturing and stapling. This is because even if gaps are left in the construction there will still be spaced connections along the length of the skin separation sufficient to provide support for the skin and effective closure. The gaps may also be used to accommodate drain tubes and other devices as may be required and they can be used to administer medications.

Figure 8:
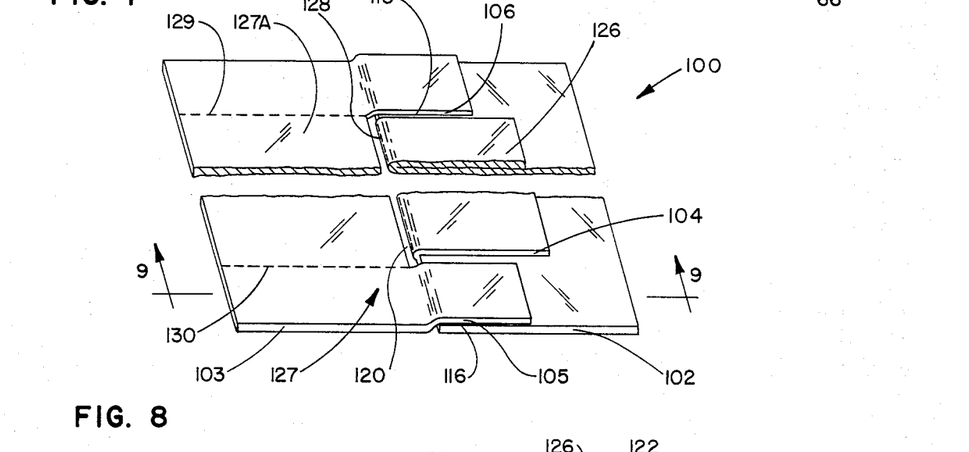
FIG. 8 is an enlarged fragmentary perspective view showing another embodiment of the present device.
Figure 9:
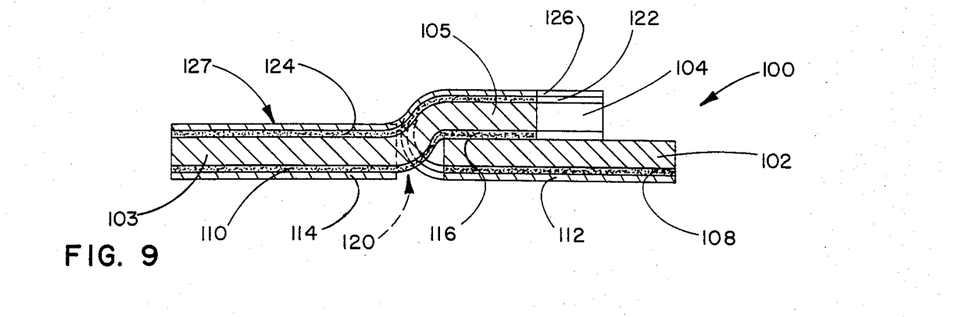
FIG. 9 is an enlarged cross-sectional view taken on line 9—9 of FIG. 8.

In FIG. 8, item 100 shows yet another embodiment of the subject construction. The device 100 includes opposite sheet portions 102 and 103, with the sheet portion 102 including folded back sheet portion 104 adhesively attached thereto and sheet portion 103 including sidewardly extending end portions 105 and 106. As in the embodiment 10, the device 100 as shown in FIG. 9 includes lower adhesive layers 108 and 110 with protective coverings or layers 112 and 114, respectively. The device 100 differs from the device 10, however, in that the end portions 105 and 106 of the sheet portion 103 are fixedly attached to sheet portion 102, at least along part of the length thereof, as at locations 116 and 118 in FIG. 8. The sheet portions 102 and 103 are not attached or connected to each other except by the end portions 105 and 106, but are adjacent each other to form a narrow separation or slot therebetween, indicated at 120 in FIGS. 8 and 9. The embodiment 100 is provided with upper adhesive layers 122 and 124 as shown in FIG. 9, and upper protective covers 126 and 127 respectively. The protective cover 126 and adhesive layer 122 can be extensions of the protective cover 112 and adhesive layer 108 respectively as shown in FIGS. 8 and 9 thereby reducing the cost of manufacturing since a single adhesive layer and cover layer can be placed on one side of the sheet member and then a portion thereof can be folded back and adhesively attached thereto as described previously. The coverings 126 and 112 can be separated by perforations 128 shown in FIG. 8 in order that each cover can be separately and easily removed without requiring any cutting therethrough which might damage the device. Perforations, such as perforations 129 and 130, can also be included in cover layer 127 so that only portion 127A of cover layer 127, which is the portion that will subsequently be covered by sheet portion 104, need be uncovered. Thus clothing, linens and so on need not be exposed to any adhesive located on the other parts of sheet portion 103 including on the elongated ends 105 and 106 as would be the case were a single cover layer utilized over the adhesive located on the entire upper surface thereof. If desired, however, a one piece upper protective cover could extend across and cover both adhesive layers 122 and 124 and may provide an advantage in locating and accurately attaching the embodiment 100 to the skin by producing a desirable holding together of the portions 103 and 104. The slot 120 in the embodiment 100 as shown in FIGS. 8 and 9 makes it easy to control the length of an incision. Depending on the width of the slot 120 it may also be easier to make an incision there along with little likelihood of damage to the closure members. Additionally, by having the end portions 105 and 106 connected to portion 102, the device 100 may provide advantages over the device 10 in that a surgeon can not only make the incision and conduct the surgery while the end portions are connected but the connected end portions will also help to keep the portions 102 and 103 in alignment for later accurate reclosing of the skin separation. Furthermore, the end connection feature reduces the possibility for skin tears at the ends of the incision. Such a construction may be especially adaptable for use in plastic surgery and other cosmetic procedures, in surgery where long incisions are made, and in situations where the chance of tearing the skin is relatively great. This includes surgery on children and infants where the skin is very fragile.

The embodiment 100 is also particularly adaptable for use in emergency medical procedures. After removal of the lower protective layers or covers 112 and 114, the sheet portions 102 and 103 may be aligned with the edges of the skin separation by aligning the slot 120 with the ends of the skin separation. Once aligned, the portions of the sheet portion 102 underlying at least one of the end portions 105 and 106 can be adhesively attached to the skin first and thereafter the rest of the portions 102 and 103 can be attached. Subsequently, the skin separation can be effectively and accurately closed by removing the upper protective covers 126 and 127A, detaching the folded back portion 104 from the portion 102, pulling it over and across the sheet portion 103 until the skin separation is closed by having its opposite side edges brought into abutment and attaching it to the portion 103 as previously explained. The ability to be able to quickly and accurately align and adhere the embodiment 100 to the skin at the appropriate location and thereafter to quickly and accurately close the skin separation is an important advantage of the embodiment 100. The embodiment 100 may also be provided with spaced transversely extending perforations or slits in the folded back sheet portion 104 and in upper protective cover 126 similar to the perforations described in the construction shown in FIGS. 3 and 4, and it may include spaced folded back sheet portions on the separate portions 103 and 104 similar to that shown in FIGS. 6 and 7.

Figures 10, 11:
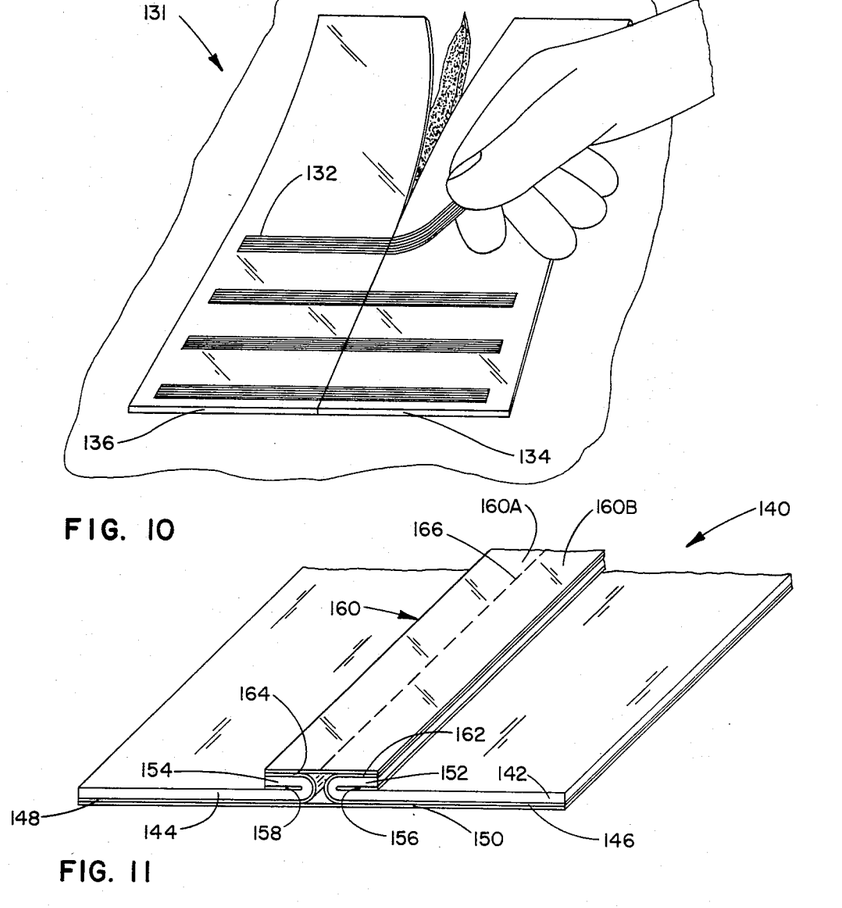
FIG. 10 is a perspective view showing yet another embodiment of the device adhesively attached to the skin at an intermediate stage of manipulation to effect skin closure.
FIG. 11 is an enlarged fragmentary perspective view showing a still further embodiment of the present device.

It is also possible and contemplated that instead of providing a folded back sheet portion as found in the previously described embodiments, an embodiment 131 could provide one or more separate adhesive members or portions such as adhesive strips 132 as shown in FIG. 10 which would be adhered to the upper surfaces of adjacent sheet members 134 or 136 which have been adhesively attached to the skin along opposite sides of a skin separation. When applied, the strips 132 are first attached adhesively to one of the sheets 134 or 136 and thereafter extended over and after being pulled to bring the edges of the sheets 134 and 136 together, adhered to the other sheet member to complete the closure. Such additional, separate strips 132 could each be provided with an adhesive layer on one surface thereof which could be covered by a removable protective covering that would be removed prior to use. The advantages of this construction over the use of strips 132 by themselves is that the sheets 134 and 136 provide good support for the skin and enable the skin separation to be reopened and closed without having to detach or reattach anything to the skin itself.

Figure 12:
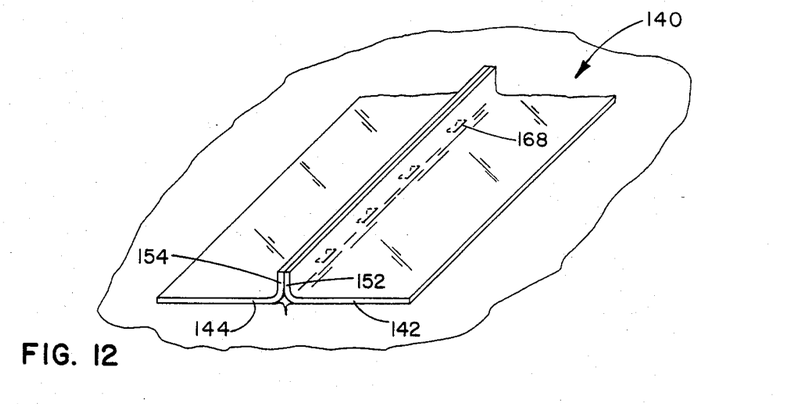
FIG. 12 is a fragmentary perspective view of the device of FIG. 11, shown adhesively attached to the skin and connected to effect closure of a skin separation.

A further embodiment 140 of the present construction is shown in FIGS. 11 and 12. Embodiment 140 includes adjacent similar sheet members 142 and 144 with lower adhesive layers 146 and 148 and a protective covering 150 located thereon similar to that described in connection with the embodiment 10. Embodiment 140 differs from embodiment 10 by including folded back flange portions 152 and 154 adhesively attached respectively to each of the sheet members 142 and 144 as by adhesive layers 156 and 158. A protective covering 160 is attached to the upper surfaces of flanges 152 and 154 by adhesive layers 162 and 164. A single line of perforations, such as perforations 166 shown in FIG. 11, can be provided in protective covering 160, dividing it into segments 160A and 160B so that the segments 160A and 160B can be separated and an incision made, while the adhesive layers 162 and 164 remain protected. Use of a one piece cover 160 also helps to hold the members 142 and 144 together so that the device may be attached accurately to the skin. Alternatively, members 142 and 144 can be formed to include separate protective coverings located over adhesive layers 146 and 148 that extend to cover adhesive layers 162 and 164 respectively on the flange portions 152 and 154. Such wrap-around coverings could be perforated along the length thereof where the flange portions fold back from the sheet members in order that the coverings over the adhesive layers 146 and 148 could be removed separately from the coverings over the adhesive layers 162 and 164. The sheet members 152 and 154 can be adhesively attached on opposite sides of a skin separation, incision, or location where one desires to make an incision, once the protective covering 150 has been removed. Thereafter, the covering 160 is separated along perforations 166, the incision made, the cover segments 160A and 160B removed and the flanges 152 and 154 detached from their respective sheets and moved towards each other and pressed together so that the now adjacent adhesive layers 162 and 164 can hold the flanges 152 and 154 together. However, to assure that the flanges don't pull apart when in use they can be more firmly attached to each other by means such as by staples 168 as shown in FIG. 12, thereby completing the closing of the skin separation or incision. By stapling through the flanges one is able to obtain a strong connection between the flange portions 152 and 154, and without having to staple into or through the skin with the accompanying pain and discomfort that this causes. The flanges 152 and 154 could also be sewed or sutured together as opposed to suturing the skin itself if desired. Such a construction may be especially suited for emergency room settings where speed in closing skin separations is required. The slight gap between adjacent sheet members and flange portions can serve as a guide for a scapel when an incision is being made. The sheet members, including the flange portions, are perferably constructed of a relatively flexible material that may be somewhat resilient, such as being constructed of certain types of plastics.

It should be readily apparent from the above description that one of the major advantages of the subject constructions in addition to their ease of use and application is their relatively simple and inexpensive construction using known materials and known manufacturing processes. The subject constructions also provide strong coupling of the opposite skin edges along a skin separation and the devices provide the option of re-opening a skin separation for some purpose if desired. This can be easily done especially if the adhesive for attaching to the skin and the adhesive for attaching the folded over portion are properly selected. Known techniques that use suturing and stapling on the other hand fasten skin portions only at spaced locations therealong by means that engage very little of the skin, are relatively subject to skin tears, and are uncomfortable to the patent. The subject constructions on the other hand maintain the skin edges together along the length of the skin separation and do so while maintaining the skin edges in close, accurate alignment. This in turn makes for a strong bond along the skin edges and reduces the formation of scar tissue which is normally occasioned during the healing process. Another advantage is that the subject constructions provide a strong, yet flexible, bond which enables patient movement without undue stress on the skin or on the subject device. In addition, because the subject constructions are preferably made of relatively thin, flexible materials, once applied, and when holding the opposite edges of a skin separation together, the subject constructions retain the ability to bend and flex with the skin, thereby reducing or minimizing any requirement to immobilize the injured part and reducing any discomfort that might be occasioned to the patient. The fact that most forms of the subject devices lie flat against the skin and follow the contour of the body also means that they are less likely to rub or scratch on clothing being worn by the patient.

Thus there has been shown and described novel skin closure means which have wide use and application and are particularly adaptable for use in emergency medical care situations, post-mortem surgical procedures and for other surgical procedures, and which may also serve as a means for guiding the edge of an instrument for making or cutting through skin and for rejoining skin that has been separated. The constructions disclosed fulfill all of the objects and advantages sought therefor. It will be apparent to those skilled in the art after a review of this description, however, that many other changes, modifications, variations, and other uses and applications for the subject devices, in addition to those which have been disclosed, are possible and contemplated. All such changes, modifications, variations, and other uses and applications which do not depart from the spirit and scope of the invention are deemed to be covered by the invention which is limited only by the claims which follow.

What is claimed is:

1. A device for closing a skin separation comprising first and second sheet members each having opposite surfaces and means forming a side edge therealong, the means forming a side edge along the first sheet member for extending along one side of a skin separation to be closed and the means forming a side edge along the second sheet member for extending along the other side of the skin separation to be closed, said first sheet member having an adhesive on one of the opposite surfaces for attaching it to a skin surface with the side edge thereon extending along one side of the skin separation to be closed, said second sheet member having a flap portion attached thereto along the side edge thereof to form a continuation of the second sheet member, the said means forming the side edge of the second sheet member being formed by folding the flap portion back on the second sheet member to define a folded sheet edge therealong, said flap portion being movable relative to the second sheet member between the folded back position thereof in surface to surface contact with the second sheet member and a second position bridging the skin separation and movable into surface to surface contact with the first sheet member, means on one opposite surface of the second sheet member for adhesively attaching it to the skin with the folded side edge thereof extending along the other side of the skin separation to be closed, and means for attaching the flap portion to the first sheet member in the second position thereof.

2. The device of claim 1 including means to attach the flap portion to the second sheet member in the first position thereof.

3. The device of claim 1 including a protective covering for the skin attaching adhesive on said first and second sheet members.

4. The device of claim 1 including an adhesive and a protective covering for both opposite surfaces of the first sheet member.

5. The device of claim 4 wherein the flap portion has an adhesive on the surface thereof movable into engagement with the first sheet portion in the second position thereof.

6. The device of claim 1 wherein the first and second sheet members are formed of a flexible material.

7. The device of claim 1 wherein the first and second sheet members are formed of flexible, open netting material.

8. Means to close a skin separation by bringing together skin portions along opposite sides of the separation comprising a sheet member formed by first and second sheet portions of flexible material, each of said sheet portions having opposite surfaces and each of said sheet portions having a side edge for positioning extending along respective opposite sides of a skin separation to be closed, a layer of an adhesive on corresponding surfaces of each of said sheet portions for attaching the respective sheet portions to a skin surface at locations extending along opposite sides of the skin separation to be closed, a flap portion of said first sheet portion foldable back against said first sheet portion to form a folded edge extending along and defining the aforesaid side edge thereof, means between the flap portion of said first sheet portion and the first sheet portion to hold them together in folded condition, the means holding the flap portion to the first sheet portion being separable for movement of the flap portion to an unfolded position with respect thereto and to a position extending over and across the skin separation and over a portion of said second sheet portion, and means for attaching the flap portion to the second sheet portion to hold the first and second sheet portions and the opposite side edges of the skin separation together.

9. The skin closure means of claim 8 including a layer of adhesive provided on both opposite surfaces of said second sheet portion.

10. The skin closure means of claim 8 including a removable protective cover member extending over the adhesive layers on the corresponding surfaces of each of the first and second sheet portions.

11. The skin closure means of claim 8 including an adhesive layer extending over opposite surfaces of the second sheet portion and over opposite surfaces of the first sheet portion including the flap portion, a first protective cover member extending over the adhesive layers on corresponding surfaces of the first and second portions, and a second protective cover member extending over the adhesive layer on the opposite surface of the second sheet portion and over the corresponding opposite surface of the flap portion of the first sheet portion.

12. The skin closure means of claim 8 wherein the first and second sheet portions are formed of a perforated material.

13. The skin closure means of claim 8 wherein the first and second portions are formed of an open netting material.

14. Skin closure means for closing a skin separation having adjacent side edges comprising a pair of sheet members formed of flexible material characterized by being able to intimately conform to a skin surface, each of said sheet members having opposite surfaces and a side edge, the side edges on the respective sheet members being adapted to be adjacent to one another, a corresponding one of said opposite surfaces of each member having an adhesive substance thereon to enable it to adhesively attach to a skin surface with the adjacent side edges extending along the respective side edges of the skin separation when the skin separation is closed, and means for cooperatively engaging the respective sheet members with the side edges thereof and with the side edges of the skin separation attached thereto in position closing the skin separation, the means for cooperatively engaging the respective sheet members including a flap portion forming a continuation of one of said sheet members along the side edge thereof.

15. The skin closure means of claim 14 including means for adhesively attaching the flap portion to the other sheet member.

* * * * *